United States Patent
Dohi et al.

(10) Patent No.: US 10,240,092 B2
(45) Date of Patent: Mar. 26, 2019

(54) COAL MIXTURE, METHOD FOR MANUFACTURING COAL MIXTURE, AND METHOD FOR MANUFACTURING COKE

(71) Applicant: JFE STEEL CORPORATION, Tokyo (JP)

(72) Inventors: Yusuke Dohi, Fukuyama (JP); Kiyoshi Fukada, Fukuyama (JP); Takashi Matsui, Fukuyama (JP); Mikiya Nagayama, Kawasaki (JP); Narumi Nanri, Fukuyama (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days.

(21) Appl. No.: 15/129,983

(22) PCT Filed: Mar. 23, 2015

(86) PCT No.: PCT/JP2015/001613
§ 371 (c)(1),
(2) Date: Sep. 28, 2016

(87) PCT Pub. No.: WO2015/146122
PCT Pub. Date: Oct. 1, 2015

(65) Prior Publication Data
US 2017/0137716 A1    May 18, 2017

(30) Foreign Application Priority Data
Mar. 28, 2014    (JP) .................................. 2014-067431

(51) Int. Cl.
*C10L 5/00*    (2006.01)
*G01N 11/02*    (2006.01)
(Continued)

(52) U.S. Cl.
CPC ................ *C10B 57/04* (2013.01); *C10L 5/04* (2013.01); *C10L 9/08* (2013.01); *C21B 5/007* (2013.01);
(Continued)

(58) Field of Classification Search
CPC ......... C10B 53/04; C10B 53/06; C10B 57/04; C10B 57/06; G01N 11/02; G01N 11/04; G01N 33/222; C10L 5/00; C10L 5/04
See application file for complete search history.

(56) References Cited

U.S. PATENT DOCUMENTS 9,102,892 B2 *   8/2015   Dohi .................. C10B 57/06
9,340,740 B2 *   5/2016   Dohi .................. C10B 45/00
(Continued)

FOREIGN PATENT DOCUMENTS

CN   1286722 A    3/2001
EP   1026223 A1   8/2000
(Continued)

OTHER PUBLICATIONS

Espacenet English Translation of Izumi et al. (JP 2012-072391 (A)).*
(Continued)

*Primary Examiner* — Jonathan Miller
*Assistant Examiner* — Jonathan Luke Pilcher
(74) *Attorney, Agent, or Firm* — Oliff PLC (57) ABSTRACT

A coal mixture is provided that maintains a high level of coke strength after carbonization, even where coal having an excessively large permeation distance is used in a large amount. The coal mixture includes large-permeation-distance coal and permeation-distance-decreasing coal. The permeation-distance-decreasing coal has a mean maximum vitrinite reflectance Ro of 1.25% or more and a total inert amount TI of 30 vol. % or less. The blending ratio of the
(Continued)

permeation-distance-decreasing coal in the coal mixture is in a range derived by multiplying the blending ratio of the large-permeation-distance coal by 0.25 or more and 3.0 or less.

14 Claims, 5 Drawing Sheets

(51) Int. Cl.
| | |
|---|---|
| *G01N 11/04* | (2006.01) |
| *C10B 53/04* | (2006.01) |
| *C10B 57/04* | (2006.01) |
| *C10L 5/04* | (2006.01) |
| *C10L 9/08* | (2006.01) |
| *C21B 5/00* | (2006.01) |
| *C10L 5/02* | (2006.01) |
| *G01N 33/22* | (2006.01) |

(52) U.S. Cl.
CPC .............. *C10B 53/04* (2013.01); *C10L 5/00* (2013.01); *C10L 5/02* (2013.01); *C10L 2290/06* (2013.01); *G01N 11/02* (2013.01); *G01N 11/04* (2013.01); *G01N 33/222* (2013.01)

(56) References Cited

U.S. PATENT DOCUMENTS

| | | | | |
|---|---|---|---|---|
| 9,708,558 | B2* | 7/2017 | Dohi | ............ C10B 57/04 |
| 2013/0255142 | A1* | 10/2013 | Dohi | ............ C10B 57/06 |
| | | | | 44/550 |
| 2014/0144071 | A1* | 5/2014 | Dohi | ............ C10B 45/00 |
| | | | | 44/607 |
| 2015/0007493 | A1* | 1/2015 | Dohi | ............ C10B 57/04 |
| | | | | 44/595 |

FOREIGN PATENT DOCUMENTS

| | | | | |
|---|---|---|---|---|
| JP | 2010043196 | A | 2/2010 | |
| JP | 2012-072388 | A | 4/2012 | |
| JP | 2012-072389 | A | 4/2012 | |
| JP | 2012072391 | A * | 4/2012 | ............ C10B 57/04 |
| JP | 5062353 | B2 | 10/2012 | |
| JP | 5071578 | B2 | 11/2012 | |
| JP | 5152378 | B2 | 2/2013 | |
| JP | 2013-181048 | A | 9/2013 | |
| WO | 2013/128866 | A1 | 9/2013 | |

OTHER PUBLICATIONS

Espacenet English Abstract of Izumi et al. (JP 2012-072391 (A)).*
Berkutov et al., "Influence of the Batch's Ash Content on Coke Quality (CRI and CSR))", ISSN 1068-364X, Coke and Chemistry, 2013, vol. 56, No. 6, pp. 201-203. © Allerton Press, Inc., 2013.*
"Methods for the petrographic analysis of bituminous coal and anthracite". 1992. International Organization for Standardization.*
May 12, 2015 International Search Report issued in International Patent Application No. PCT/JP2015/001613.
Sakamoto et al.: CAMP-ISIJ, vol. 11 (1998), p. 98.
Arima et al.: Tetsu-to-Hagane, vol. 82 (1996), p. 409.
Nomura et al.: CAMP-ISIJ, vol. 4 (1991), p. 132.
Miyazu et al.: "Nippon Kokan Technical Report", vol. 67 (1975), pp. 125-137.
Jun. 21, 2016 Notice of Allowance issued in Japanese Patent Application No. 2016-510023.
Mar. 3, 2017 Search Report issued in European Patent Application No. 15769682.4.
May 26, 2016 Office Action issued in U.S. Appl. No. 14/375,271.
Dec. 12, 2017 Office Action issued in European Patent Application No. 15 769 682.4.
Aug. 10, 2017 Office Action issued in Korean Patent Application No. 2016-7029089.
Aug. 17, 2018 Office Action issued in Chinese Patent Application No. 201580016284.6.

* cited by examiner

COAL MIXTURE, METHOD FOR MANUFACTURING COAL MIXTURE, AND METHOD FOR MANUFACTURING COKE

TECHNICAL FIELD

The present disclosure relates to a coal mixture which is used as a raw material capable of manufacturing coke having a high strength, and relates to a method for manufacturing the coal mixture and to a method for manufacturing coke.

BACKGROUND ART

In the case where molten pig iron is manufactured by using a blast furnace, iron ore and coke are charged into the blast furnace in order to pack each of them in the form of a layer; the iron ore and coke are heated with high-temperature hot air which is blown into the blast furnace through tuyeres; and the iron ore is reduced with CO gas which is generated from the coke. In order to stably operate the blast furnace, since it is necessary to achieve gas permeability and liquid permeability in the furnace, it is indispensable for the operation coke having various excellent properties such as strength, particle diameter, and strength after a reaction. In particular, coke strength such as drum strength is an important property.

The strength of coke is usually determined and controlled by performing a drum strength test prescribed in JIS K 2151 or the like. Coal particles melt and adhere to each other to form coke in a carbonization process. Therefore, the difference of thermoplasticity of coal strongly influences the strength of coke, and it is necessary to evaluate the thermoplasticity of coal from the viewpoint of controlling coke strength. "Thermoplasticity" refers to the quality of melting when coal is heated, and the thermoplasticity is usually evaluated in terms of fluidity, viscosity, adhesiveness, dilatability, permeability and/or the like of a thermoplastic material.

Typical example of a method for determining fluidity in a melting process among the indexes of the thermoplasticity of coal is a coal fluidity testing method using a Gieseler plastometer method prescribed in JIS M 8801. The Gieseler plastometer method involves: charging crushed coal particles having a particle diameter of 425 μm or less into a specified crucible; heating the sample at a specified heating rate; and determining the rotational speed of a stirring rod to which a specified torque is applied. The method indicates the thermoplasticity of the sample in terms of dial division per minute (ddpm). Known examples of other methods for evaluating thermoplasticity include a method for measuring torque by using a constant rotational speed method, a method for measuring viscosity by using a viscoelastometer, and a dilatometer method prescribed in JIS M 8801.

In contrast with a coal fluidity testing method, Patent Literature 1 proposes a method for evaluating thermoplasticity under a condition in which an environment to which thermoplastic coal is exposed in a coke oven is considered. That is, the method takes consideration of a condition of simulating an environment where thermoplastic coal is constrained and where the thermoplastic coal moves and permeates into the surrounding defective structure. Patent Literature 1 describes that a permeation distance determined by using this method is the index of the thermoplasticity of coal different from those determined by using conventional methods. Patent Literature 1 indicates that the permeation distance influences coke strength and that there is a decrease in coke strength as a result of large pore defects being formed in the coke in the case where coal having an excessively large permeation distance is mixed in a coal blend for coke making.

In addition, Patent Literature 2 discloses a method which involves: specifying the range of permeation distance that may cause a decrease in the coke strength; and controlling the permeation distance of an individual coal brand which is used as a coking raw material separately or in a blend with other coal brands so as to be out of the range. The disclosed specific examples of a method for controlling permeation distance mainly include two methods. One of the examples is a method which involves mixing coal brands having different permeation distances to control permeation distance. This method is based on the fact that the permeation distance of a coal blend is almost equal to the average permeation distance of individual constituent coal brands weighted by the blending ratios of the constituent coal brands. The other one is a method which involves making coal subject to an oxidizing treatment or a weathering treatment. This method is based on the fact that it is possible to decrease the permeation distance of a raw material coal by adjusting the degree of oxidation by controlling oxidizing conditions such as temperature, time, and oxygen content. In addition, Patent Literature 3 discloses that a method for manufacturing high-strength metallurgical coke involves: specifying the range of permeation distance that may cause a decrease in the coke strength as is the case with Patent Literature 2; and controlling the particle diameter of a coal brand within the range to be smaller than a specified particle diameter before blending the coal brand in a coaking coal blend, to reduce the negative effect of the coal brand having a permeation distance which may cause a decrease in coke strength. At the result, the method manufactures high-strength metallurgical coke from the coal blend.

CITATION LIST

Patent Literature

PTL 1: Japanese Patent No. 5062353
PTL 2: Japanese Patent No. 5071578
PTL 3: Japanese Patent No. 5152378

Non Patent Literature

NPL 1: Sakamoto et al.: CAMP-ISIJ, vol. 11 (1998), p.
NPL 2: Arima et al.: Tetsu-to-Hagane, vol. 82 (1996), p.
NPL 3: Nomura et al.: CAMP-ISIJ, vol. 4 (1991), p. 132
NPL 4: Miyazu et al.: "Nippon Kokan Technical Report", vol. 67 (1975), pp. 125-137

SUMMARY

Technical Problem

As described above, since coal having an excessively large permeation distance causes a decrease in coke strength, coke is ideally manufactured with the amount of such coal added to a coal blend being as small as possible. However, in contemporary coke making, there is a trend toward blending plural kinds of coal of many coal mining areas and many coal brands from the viewpoint of stably sourcing materials. Therefore, there is a demand for using any kind of coal in a large amount even in the case where the coal has an excessively large permeation distance. Although the conventional techniques describe methods for using coal having an excessively large permeation distance, the conventional techniques have the following problems.

Patent Literature 1 describes blending plural brands of coal and preventing the blending ratio (sometimes, also simply referred to as "ratio" or referred to as "mixing ratio") of coal having a large permeation distance from excessively increasing, in order to prevent the permeation distance of a coal blend from excessively increasing so that there is no decrease in coke strength. However, Patent Literature 1 does not mention criteria regarding the properties of other brands of coal which may be combined with the coal having a large permeation distance or regarding an allowable blending ratio of coal having a large permeation distance.

Patent Literature 2 describes a method for preparing a coal mixture having a preferable permeation distance by mixing coal brands having different properties. This method is under the assumption that the determined permeation distance of a coal blend is almost equal to the average permeation distance of individual constituent coal brands weighted by the blending ratios of the constituent coal brands. However, in fact, there is a combination of coal brands in which the weighted average permeation distance and the determined permeation distance are not almost the same, and therefore it is not practically possible to apply the technique according to Patent Literature 2 in order to control the permeation distance of a coal mixture containing such a combination. Moreover, Patent Literature 2 does not mention and suggest a combination of coal brands in which the weighted average permeation distance and the determined permeation distance are not almost the same. In addition, Patent Literature 3 discloses a method which involves controlling the particle diameter of a coal brand having a large permeation distance to be smaller than a specified particle diameter before blending the coal brand in a coking coal blend, to reduce the negative effect of the coal brand. However, since it is necessary to increase a pulverizing power when the coal is pulverized in this method, there is an increase in coke making costs due to an increase in pulverizing costs.

As described above, the conventional techniques are restricted by the condition that, in the case where coal having an excessively large permeation distance is used as a raw material for coke as it is, the blending ratio of the coal may not sufficiently increase without increasing coal pulverizing costs. Therefore, a technique for using coal having an excessively large permeation distance, which may cause a decrease in coke strength, in a large amount and at low cost has not been completed from the viewpoint of manufacturing high-strength coke.

The disclosed embodiments have been completed in view of the situation described above, and an object of the present disclosure is, by solving the problems with the conventional techniques described above, to increase the amount of coal having an excessively large permeation distance, which may cause a decrease in coke strength, used with ease and at low cost.

Solution to Problem

The present inventors diligently conducted investigations, in which large-permeation-distance coal is defined as a coal which exceeds the standard according to Patent Literature 2 and Patent Literature 3, and the properties of coal which reduce the influence of the large-permeation-distance coal which decreases coke strength are studied. Specifically, the present inventors completed the present disclosure by focusing on the additivity of the permeation distances of plural coal brands and by diligently conducted investigations regarding such a property. "Additivity of permeation distance" indicates how likely the practically determined permeation distance of a coal blend containing plural coal brands is to be equal to the average permeation distance of the individual coal brands weighted by the blending ratios of the individual coal brands in the coal blend. Here, a case where the determined permeation distance is close to the weighted average permeation distance is referred to as the case where additivity is observed (good), and a case where the determined value is different from the weighted average value is referred to as the case where additivity is not observed (poor).

The subject matter of the disclosed embodiments may include as follows.

[1] A coal mixture comprising: large-permeation-distance coal; and permeation-distance-decreasing coal, wherein, mass fraction of the permeation-distance-decreasing coal in the coal mixture is in a range derived by multiplying mass fraction of the large-permeation-distance coal by 0.25 or more and 3.0 or less, the permeation-distance-decreasing coal has a mean maximum vitrinite reflectance Ro of 1.25% or more and a total inert amount TI of 30 vol. % or less, a permeation distance (mm) which is determined by following steps of:

placing a material having through-holes penetrating from upper surface to lower surface of the material on the top of a coal sample packed in a container;

heating the coal sample to permeate into the through-holes; and determining a distance over which the coal permeates into the through-holes as the permeation distance (mm); and, the large-permeation-distance coal has the permeation distance (mm) which is more than value of permeation distance derived by using following equation [I]:

$$\text{permeation distance} = 1.3 \times a \times \log MF \qquad [\text{I}]$$

where MF is the Gieseler maximum fluidity (ddpm) of coal and a is a constant defined as a coefficient of the common logarithm log MF of Gieseler maximum fluidity MF multiplied by a value in the range of 0.7 or more and 1.0 or less, when a regression line that passes through the origin is drawn based on data sets of the determined value of permeation distance (mm) and log MF of at least one of coal brands having a log MF of less than 2.5.

[2] The coal mixture according to item[1], wherein the constant a is a constant defined as a coefficient of the common logarithm log MF of Gieseler maximum fluidity MF multiplied by a value in the range of 0.7 or more and 1.0 or less, when a regression line that passes through the origin is drawn based on data sets of the determined value of permeation distance and log MF of at least one of coal brands having a log MF of more than 1.75 and less than 2.50.

[3] A coal mixture comprising: large-permeation-distance coal; and permeation-distance-decreasing coal, wherein, mass fraction of the permeation-distance-decreasing coal in the coal mixture is in a range derived by multiplying mass fraction of the large-permeation-distance coal by 0.25 or more and 3.0 or less, the permeation-distance-decreasing coal has a mean maximum vitrinite reflectance Ro of 1.25% or more and a total inert amount TI of 30 vol. % or less, a permeation distance (mm) which is determined by following steps of:

placing a material having through-holes penetrating from upper surface to lower surface of the material on the top of a coal sample packed in a container;

heating the coal sample to permeate into the through-holes; and determining a distance over which the coal permeates into the through-holes as the permeation distance (mm); and, the large-permeation-distance coal has a permeation distance (mm) which is more than the value of the permeation distance derived by using equation [II]:

$$\text{permeation distance} = a' \times \log MF + b \qquad [II],$$

where MF is the Gieseler maximum fluidity (ddpm) of coal, a' is a constant defined as a coefficient of the common logarithm log MF of a Gieseler maximum fluidity MF multiplied by a value in the range of 0.7 or more and 1.0 or less, when a regression line that passes through the origin is drawn based on data sets of the determined value of permeation distance (mm) and log MF of at least one of coal brands having a log MF of less than 2.5, and b is a constant defined as a value equal to or more than the average value of the standard deviation of permeation distance and equal to or less than a value derived by multiplying the average value by 5, when determination is performed plural times for the same sample of one or more kinds of coal selected from among the coal brands which are used for deriving the regression line.

[4] The coal mixture according to item [3] above, wherein the constant a' is a constant defined as a coefficient of the common logarithm log MF of Gieseler maximum fluidity MF multiplied by a value in the range of 0.7 or more and 1.0 or less, when a regression line is drawn based on data sets of the determined value of permeation distance and log MF of at least one of coal brands having a log MF of more than 1.75 and less than 2.50.

[5] A coal mixture comprising: large-permeation-distance coal; and permeation-distance-decreasing coal, wherein, mass fraction of the permeation-distance-decreasing coal in the coal mixture is in a range derived by multiplying mass fraction of the large-permeation-distance coal by 0.25 or more and 3.0 or less, the permeation-distance-decreasing coal has a mean maximum vitrinite reflectance Ro of 1.25% or more and a total inert amount TI of 30 vol. % or less, the large-permeation-distance coal having a permeation distance which is determined by following steps (1) to (4), of 15 mm or more:

(1) pulverizing coal so that particles having a particle diameter of 2 mm or less constitute 100 mass % of the sample and packing the pulverized coal into a container so that the bulk density is 0.8 g/cm³ and the layer thickness is 10 mm, to prepare a coal sample;

(2) placing glass beads having a diameter of 2 mm on the top of the coal sample so that the thickness of the glass bead layer is more than a permeation distance;

(3) heating the coal sample from room temperature to a temperature of 550° C. at a heating rate of 3° C./min in an inert gas atmosphere with a load of 50 kPa being applied to the top of the glass bead layer so that the coal sample melts and permeates into the glass bead layer, and (4) determining the permeation distance (mm) of the coal sample which has permeated into the glass bead layer.

[6] The coal mixture according to any one of items [1] to [5] above, wherein the content of the large-permeation-distance coal is 30 mass % or less.

[7] A method for manufacturing the coal mixture according to any one of items [1] to [6] above, the method including steps of: preparing the large-permeation-distance coal and the permeation-distance-decreasing coal; and mixing the large-permeation-distance coal and the permeation-distance-decreasing coal so that the content of the permeation-distance-decreasing coal is in a range derived by multiplying the content of the large-permeation-distance coal by 0.25 or more and 3.0 or less.

[8] A method for manufacturing coke by using the coal mixture according to any one of items [1] to [6] above, the method including steps of: preparing a coal blend from a single coal mixture or a mixture of a coal mixture and other coal; charging the coal blend into a coke oven; and performing carbonization.

Advantageous Effects

According to the present disclosure, even in the case where large-permeation-distance coal is used for a coking coal blend, merely blending coal which reduces the influence of the large-permeation-distance coal makes it possible to obtain a coal mixture which composes a coal blend and which makes it possible to increase coke strength after the carbonization of the coal blend, without performing any further special treatment. Therefore, it is possible to use large-permeation-distance coal in a larger amount than ever before, and, it is possible to control coal blending conditions in order to maintain a high level of coke strength which is achieved by carbonizing a coal blend containing the coal mixture described above.

DESCRIPTION OF EMBODIMENTS

The present inventors found that, as coal to be blended with large-permeation-distance coal, coal having a mean maximum vitrinite reflectance of 1.25% or more and a total inert amount TI in a petrographic analysis of 30 vol. % or less reduces the influence of the large-permeation-distance coal, which decreases coke strength, and completed the present disclosure. Hereafter, an example of the exemplary embodiments of the present disclosure will be described.

Figure 1:
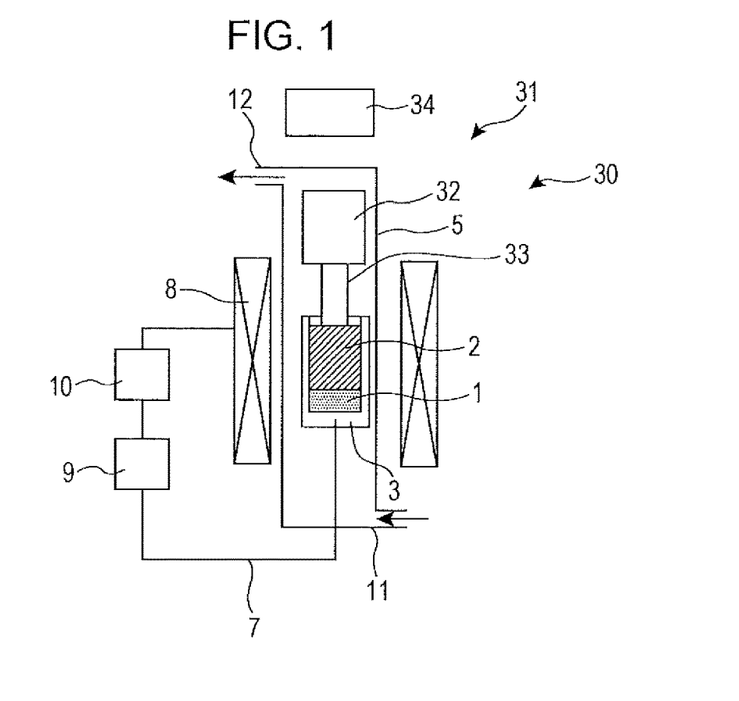
FIG. 1 is a diagram illustrating an exemplary apparatus for determining the permeation distance of a coal sample by applying a constant load onto the coal sample and a material having through-holes penetrating from the upper surface to the lower surface.

The method for determining the permeation distance of coal described in Patent Literature 1 will be briefly described. It is possible to refer to Patent Literature 1 regarding the details of a method for determining permeation distance. FIG. 1 is a diagram illustrating an exemplary apparatus for determining the permeation distance of a coal sample by applying a constant load onto the coal sample and a material having through-holes penetrating from the upper surface to the lower surface. A determining apparatus 30 has a container 3 for containing constituent coal of a coal blend or the like, a sleeve 5 for containing the container 3, a heating device 8 placed outside the sleeve 5, and a loading device 31.

Charging coal or the like into the container 3 forms the layer of a sample 1. Placing a material 2 having through-holes penetrating from the upper surface to the lower surface on the top of the layer of the sample 1 forms the layer of the material 2. Subsequently, heating the sample 1 to a temperature within or higher than a thermoplastic temperature range by using the heating device 8 allows the sample 1 to melt and to permeate into the material 2, thereby determining permeation distance. Examples of the form of the material 2 include an integrated material having through-holes and a particle-packed layer. Examples of an integrated material having through-holes include one having circular through-holes, one having rectangular through-holes, and one having irregular-shaped through-holes. Examples of a particle-packed layer are roughly classified into a packed layer of spherical-shaped particles and a packed layer of non-spherical-shaped particles, and examples of a packed layer of spherical-shaped particles include one composed of packing particles such as beads.

The sleeve 5 has a gas inlet port 11 and gas outlet port 12. Charging an inert gas into the sleeve 5 through the gas inlet port 11 has the sleeve 5 filled with the inert gas to make an atmosphere of the container 3 into an inert gas atmosphere. The inert gas in the sleeve 5 is discharged through the gas outlet port 12.

The loading device 31 has a weight 32, a dilatation-detecting rod 33, and a displacement sensor 34.

Determination of dilatation involves steps of: placing the dilatation-detecting rod 33 on the upper surface of the material 2 illustrated in FIG. 1; placing the weight 32 for applying load on the upper end of the dilatation-detecting rod 33; and placing the displacement sensor 34 thereon, thereby determining dilatation. A displacement sensor which is applicable in the dilatation range (−100% to 300%) of the sample may be used as the displacement sensor 34. Since it is necessary to keep the inside of the heating system in an inert gas atmosphere, it is appropriate to use a contactless-type displacement sensor, and it is preferable to use an optical displacement sensor. It is preferable to use a nitrogen gas atmosphere as an inert gas atmosphere. In the case where the material 2 is a particle-packed layer, there is a possibility that the dilatation-detecting rod 33 be buried in the particle-packed layer, and therefore it is preferable that a plate is interposed between the material 2 and the dilatation-detecting rod 33.

It is preferable that the applied load be uniformly put on the upper surface of the material 2, and it is preferable that the load be 5 kPa to 80 kPa, preferably 15 kPa to 55 kPa, or most preferably 25 kPa to 50 kPa. It is preferable that the load be set on the basis of the swelling pressure of a thermoplastic layer in a coke oven. It is most preferable that a load is slightly higher than the swelling pressure in the coke oven, that is, a pressure of about 25 kPa to 50 kPa be used as a determination condition, in view of result of investigations regarding repeatability of determination results and statistical power of difference among various brands of coal.

A temperature controller 10 is connected to the heating device 8; a thermometer 7 is fitted to the container 3; and a temperature detector 9 is connected to the thermometer 7. The temperature detector 9 detects the temperature of the thermometer 7; the detected temperature data is transmitted to the temperature controller 10; and the heating temperature is controlled by the heating device 8 on the basis of the temperature data. As the heating device 8, it is preferable to use a heating device which can be heated at a specified heating rate. Specific examples of the heating device include an external-heating type device such as an electric furnace and one composed of a conductive container and a high-frequency induction heater and an internal-heating type device such as one using microwave. In the case where an internal-heating type device is used, it is necessary to cause the temperature inside the sample to be homogenized, and thus it is preferable, for example, to increase the thermal insulation capability of a container.

It is preferable that the heating rate be equal to the heating rate of coal in a coke oven in order to simulate the thermoplastic behavior of coal in the coke oven. Although the heating rate of coal in a thermoplastic temperature range in a coke oven varies in accordance with the position in the coke oven and operation conditions, the heating rate is about 2° C./min to 10° C./min, it is preferable that an average heating rate be 2° C./min to 4° C./min, or most preferably about 3° C./min. However, in the case of coal having low fluidity such as non- or slightly-caking coal, permeation distance and dilatation are small if the heating rate is 3° C./min, and thus it may be difficult to detect these properties. It is generally known that there is an increase in Gieseler plastometer fluidity when coal is rapidly heated. For example, in the case that coal has a low fluidity corresponding to a permeation distance of 1 mm or less, determination may be performed at a raised heating rate of 10° C./min to 1000° C./min in order to increase detection sensitivity.

Appropriate heating temperature range is not less than temperature within a thermoplastic temperature range of coal, since heating is performed in order to evaluate the thermoplasticity of coal. In consideration of the thermoplastic temperature range of coking coal, it is appropriate that heating be performed in a temperature range of 0° C. to 550° C., or preferably in a temperature range of 300° C. to 550° C., which is the thermoplastic temperature range of coal, at the heating rate described above.

A material such as coal to be used as the sample 1 is pulverized. Thereafter, the pulverized coal is charged with a specified density to have a specified layer thickness. It is preferable that the proportion of particles having a pulverized particle diameter of 3 mm or less to the whole coal to be charged into a coke oven be about 70 mass % to 80 mass %. It is particularly preferable that the pulverized particle diameter of all the particles be 2 mm or less in consideration of determination by a small apparatus. The density of the pulverized material may be controlled to be 0.7 g/cm$^3$ to 0.9 g/cm$^3$ in accordance with the bulk density in a coke oven. And, it is particularly preferable that the density be 0.8 g/cm$^3$ in view of the results of investigations regarding repeatability and statistical power (in terms of density on a dry basis in any case). In addition, the layer thickness of the sample 1 may be controlled to be 5 mm to 20 mm on the basis of the thickness of a thermoplastic layer in a coke oven.

And it is preferable that the thickness be 10 mm in view of the results of investigations regarding repeatability and statistical power.

In the case where a glass bead layer having a uniform particle diameter is used as the material 2, in order to achieve a preferable permeation coefficient described above, it is preferable to select glass beads having a diameter of 0.2 mm to 3.5 mm, or most preferably 2 mm.

It is essentially preferable that the permeation distance of thermoplastic coal be continuously determined always in a heating process. However, it is difficult to always perform determination due to the influence of, for example, tar which is generated from the sample. Since swelling and permeation phenomena of coal due to heating are irreversible, once swelling and permeation occur, a form obtained as a result of swelling and permeation remains even after cooling is performed. Therefore, by cooling the whole container after the permeation of thermoplastic coal has been finished, and by determining a permeation distance after cooling, the position to which the sample permeated during the heating process may be defined as the determined permeation distance. For example, by taking out the material 2 from the container after cooling has been performed, it is possible to directly determine the permeation distance by using a vernier micrometer or a ruler. In addition, in the case where particulate materials are used for the material 2, a thermoplastic material which has permeated into interparticle pores makes all of the particles in the permeated portion adhere to each other. Therefore, if the relationship between the mass and height of a particle-packed layer has been derived in advance, it is possible to calculate a permeation distance from the mass of the particles which adhere to each other, which is derived by determining the mass of the particles which do not adhere to each other after permeation has been finished and by subtracting the determined mass from the original mass.

Figure 2:
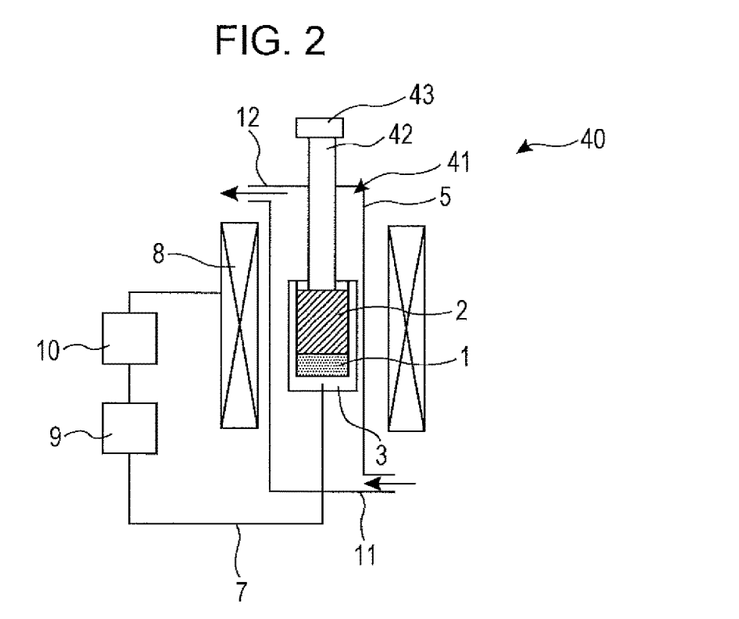
FIG. 2 is a diagram illustrating an exemplary apparatus for determining the permeation distance of a coal sample with the volume of the coal sample and a material having through-holes penetrating from the upper surface to the lower surface being kept constant.

FIG. 2 is a diagram illustrating an exemplary apparatus for determining the permeation distance of a coal sample with the volume of the coal sample and a material having through-holes penetrating from the upper surface to the lower surface being kept constant. Among the signs in FIG. 2, common constituent factors shared with FIG. 1 are denoted by the same signs as those in FIG. 1, and the description of such common constituent factors will be omitted. A determining apparatus 40 is used to determine the permeation distance of the sample 1 with the volume of the sample 1 and the material 2 being kept constant.

A loading device 41 has a pressure-detecting rod 42 and a load cell 43. FIG. 2 illustrates an apparatus with which the sample 1 is heated with the volume of the sample 1 and the material 2 being kept constant, and it is possible to determine the pressure of the sample 1 through the material 2 when permeation occurs. As illustrated in FIG. 2, by placing a pressure-detecting rod 42 on the upper surface of the material 2, and by allowing a load cell 43 to come into contact with the upper end of the pressure-detecting rod 42, it is possible to determine pressure. In order to keep the volume constant, the pressure-detecting rod 42 and the load cell 43 are fixed so as not to move vertically. Here, it is preferable that the sample 1 in the container 3, the material 2, the pressure-detecting rod 42, and the load cell 43 be brought into contact with each other in this order with no gap therebetween before heating is performed. In addition, in the case where the material 2 is a particle-packed layer, since the pressure-detecting rod 42 may be buried in the particle-packed layer, it is preferable that a plate be interposed between the material 2 and the pressure-detecting rod 42. By using other constituent factors of the determining apparatus 40 which are the same as those of the determining apparatus 30, it is possible to determine the permeation distance of the sample 1.

In the case of the conventional evaluation method of thermoplasticity using a Gieseler plastometer, it has been thought that coal particles having a high fluidity have a high capability of adhering to each other. On the other hand, according to Patent Literature 1, it is acknowledged that, although a permeation distance which is determined by using the method described above has a loose correlation with Gieseler maximum fluidity MF which is derived by using a Gieseler plastometer, even coal brands having almost the same MF have rather different permeation distances.

In addition, Patent Literature 1 indicates that, from the results of investigations regarding the relationship between permeation distance and coke strength, among coal brands having almost the same MF, there is an increase in coke strength in the case where a permeation-distance-decreasing coal brand is used, and there is a decrease in coke strength in the case where a coal brand having an excessively large permeation distance is used. According to the description of Patent Literature 1, the reason therefor is that coke strength decreases to a value smaller than the value expected from the conventional index (such as MF), because large defects are formed and a structure having brittle pore walls are formed in a coking process in the case where a coal brand having a significantly large permeation distance is added.

For the range of permeation distance of coal in which there is a decrease in coke strength, Patent Literature 2 and Patent Literature 3 propose criteria [A], [B], and [C] below.
[A] A range larger than the permeation distance which is derived by using following equation [I]:

$$\text{Permeation distance} = 1.3 \times a \times \log MF \quad\quad [\text{I}]$$

Here, MF denotes the Gieseler maximum fluidity (ddpm) of coal.

a is a constant defined as a coefficient of the common logarithm log MF of Gieseler maximum fluidity MF multiplied by a value in the range of 0.7 or more and 1.0 or less, when a regression line that passes through the origin is drawn based on data sets of the determined value of permeation distance and log MF of at least one of coal brands having a log MF of less than 2.5.
[B] A range larger than the permeation distance which is derived by using following equation [II]:

$$\text{Permeation distance} = a' \times \log MF + b \quad\quad [\text{II}]$$

Here, constant a' is a constant defined as a coefficient of the common logarithm log MF of a Gieseler maximum fluidity MF multiplied by a value in the range of 0.7 or more and 1.0 or less, when a regression line that passes through the origin is drawn based on data sets of the determined value of permeation distance and log MF of at least one of coal brands having a log MF of less than 2.5. Constant b is a constant defined as a value equal to or more than the average value of the standard deviation of permeation distance and equal to or less than 5 times the average value, when determination is performed plural times for the same sample of one or more kinds selected from among the coal brands which are used for deriving the regression line.
[C] A range in which a permeation distance, which is determined through by following steps (1) through (4), of 15 mm or more:
(1) pulverizing coal so that particles having a particle diameter of 2 mm or less constitute 100 mass % of the sample and by packing the pulverized coal into a container 3 so that the bulk density is 0.8 g/cm³ and the layer thickness is 10 mm to prepare a coal sample 1, by an apparatus such as the determining apparatus 30 in FIG. 1 which applies a constant load to the sample 1;

(2) placing material 2, that is, glass beads having a diameter of 2 mm on the top of the coal sample 1 so that the thickness of the glass bead layer is more than a permeation distance;

(3) heating the coal sample 1 from room temperature to a temperature of 550° C. at a heating rate of 3° C./min in an inert gas atmosphere with a load of 50 kPa being applied to the top of the glass bead layer so that the coal sample 1 melts and permeates into the glass bead layer; and (4) determining the permeation distance of the coal sample 1 which has permeated into the glass bead layer.

"The coefficient of log MF" in [A] and [B] above refers to the slope of a regression line which is drawn by passing through the origin under a condition that measured log MF are along the horizontal axis and measured permeation distance are along the vertical axis. That is, "The coefficient of log MF" refers to the ratio of the amount of change in permeation distance to the amount of change in log MF. The constant a or a' is defined as the value of this ratio multiplied by a value in the range of 0.7 or more and 1.0 or less, and it is possible to control the value by which this ratio is multiplied in accordance with the operational requirement. The reason why the constant a may take a value in a certain range is because, by decreasing the constant a, there is an increase in detection reliability of coal which decreases coke strength. However, in the case where the constant a is excessively small, since there is an excessive increase in the number of coal brands which are supposed to have a negative effect on coke strength, there may be a problem in that a coal brand which does not actually cause a decrease in coke strength is misunderstood as a coal brand which causes a decrease in coke strength. Therefore, the constant a is assigned to the value of the slope of the regression line multiplied by a value in the range of 0.7 or more and 1.0 or less. Therefore, in order to detect with increased reliability a coal brand which may cause a decrease in coke strength, it is appropriate that the constant a take the value of the slope of the regression line multiplied by 0.7.

The present inventors, by defining large-permeation-distance coal as coal having a permeation distance within any one of the ranges according to the criteria [A], [B], and [C] above, diligently conducted investigations regarding the properties of coal which reduces the influence of the large-permeation-distance coal, which decreases coke strength. The present inventors, focusing on the additivity of the permeation distances of plural brands of coal, diligently conducted investigations regarding such properties. First, the present inventors focused on the fact that the working examples of the conventional technique literature, that is, Patent Literature 1, indicates that the permeation distance of a coal blend has very good additivity. The properties of the coal brands which were used for the verification of the additivity of permeation distance in the working examples are given in Table 1. In the verification, four coal brands having different permeation distances were used.

TABLE 1

| | Coal Property | | | | |
|---|---|---|---|---|---|
| | Ro | logMF | VM | Ash | Permeation distance |
| | | | Unit | | |
| | % | log ddpm | mass % d.b. | mass % d.b. | mm |
| Coal V | 0.80 | 4.00 | 35.9 | 8.9 | 21.5 |
| Coal W | 1.00 | 3.08 | 27.7 | 10.4 | 12.9 |
| Coal X | 0.72 | 2.40 | 35.9 | 9.1 | 9.4 |
| Coal Y | 1.29 | 0.48 | 20.8 | 7.6 | 2.5 | d.b. refers to "on a dry basis".

On the other hand, there are many reports indicating that there is a case where the conventional index of thermoplasticity such as Gieseler plastometer fluidity or total dilatation determined by using a dilatometer method does not have additivity. Non Patent Literature 1 indicates that, the wider the difference in thermoplastic temperature range among the individual constituent coal brands of a coal blend, the more the fluidity and total dilatation of the coal blend deviate to the negative side from the weighted average values of such properties. The reason why such a behavior is shown is thought to be that, in the case where there is a difference in thermoplastic temperature range between two coal brands, one coal brand melts while the other coal brand does not melt and is in a solid state. Moreover, Non Patent Literature 2 indicates that, in the case of a coal blend to which a coal brand having a high gas pressure in a thermoplastic process is added, the expanded specific volume in a thermoplastic process deviates to the negative side from the weighted average value. Non Patent Literature 2 indicates that the reason why such a behavior is shown is because, since the coal brand having a high gas pressure compresses the surrounding coal brands when the coal brand having a high gas pressure expands, the surrounding coal brands are inhibited from expanding.

It is reported that the larger the mean maximum vitrinite reflectance Ro, the higher the gas pressure of coal, and that, the smaller the total inert amount TI determined by performing petrographic analysis, the higher the gas pressure of coal (for example, Non Patent Literature 3). In addition, in the case of raw material coal which is generally used for manufacturing metallurgical coke, the mean maximum vitrinite reflectance Ro is about 0.6% to 1.7%, and the total inert amount TI is 0% to 50%. In the present disclosure, "mean maximum vitrinite reflectance Ro" refers to the mean maximum vitrinite reflectance of coal prescribed in JIS M 8816, and "total inert amount TI" refers to the total inert amount (vol. %) in coal petrographic analysis which is calculated by equation (X) below based on the Parr equation prescribed in JIS M 8816 "Solid mineral fuels-Methods of microscopical measurement for the macerals and reflectance" and its explanation.

Total inert amount (vol. %)=fusinite (vol. %)+micrinite (vol. %)+(⅔)×semifusinite (vol. %)+mineral matter (vol. %)     (X)

The EXAMPLE 3 in Patent Literature 1 indicates that the additivity of permeation distance is valid among the four coal brands having the properties given in Table 1, and Patent Literature 1 concludes that the additivity of permeation distance is valid among coal brands having a comparatively wide range of properties. However, the present inventors, considering that, if it is possible to find a coal brand which decreases the permeation distance of a coal blend which is prepared by blending the coal brand and a large-permeation-distance coal brand to a value smaller than the weighted average permeation distance (combined permeation distance) of the individual constituent coal brands weighted by the blending ratios of the constituent coal brands, it is possible to reduce the negative effect of the large-permeation-distance coal brand, conducted additional investigations in detail by using coal brands having a wider range of properties regarding additivity in the case where this coal brand is blended with a large-permeation-distance coal brand.

From the results of the investigations, the present inventors found that, in the case where a large-permeation-distance coal brand (a coal brand within any one of the ranges according to the criteria [A], [B], and [C] above) and a coal brand having a mean maximum vitrinite reflectance Ro of 1.25% or more and a total inert amount TI of 30 vol. % or less in petrographic analysis are combined, the permeation distance of a coal blend which is prepared by mixing the coal brands is smaller than the weighted average value. Hereinafter, coal having a mean maximum vitrinite reflectance Ro of 1.25% or more and a total inert amount TI of 30 vol. % or less in petrographic analysis will be appropriately referred to as "permeation-distance-decreasing coal". The present inventors found that, in the case where the ratio of the mass of a large-permeation-distance coal brand to the mass of a permeation-distance-decreasing coal brand is 1.0:0.25 through 1.0:3.0, the permeation distance of a coal mixture which is prepared by mixing the coal brands is much smaller than the value of the combined permeation distance and that, in the case where coke is manufactured by blending the large-permeation-distance coal brand and the permeation-distance-decreasing coal brand at the same time, it is possible to reduce the influence of a coal brand having an excessively large permeation distance, which decreases coke strength. Here, it is preferable that the ratio of the mass of a large-permeation-distance coal brand to the mass of a permeation-distance-decreasing coal brand be 1.0:1.0 through 1.0:3.0.

In the case where coke is manufactured by charging a coal mixture containing permeation-distance-decreasing coal and high-permeation-distance coal as it is into a coke oven, it is preferable that the proportion of the amount of high-permeation-distance coal to the whole coal mixture (mass fraction on a dry-coal basis) be 30 mass % or less. Since the negative effect of large-permeation-distance coal on coke strength is marked in the case where the blending ratio is more than 10 mass %, it is particularly preferable that the blending ratio of large-permeation-distance coal be more than 10 mass % and 30 mass % or less. As described in the EXAMPLES below, the present inventors confirmed that, by manufacturing a coal blend from a coal mixture in which the ratio of the mass of large-permeation-distance coal to the mass of permeation-distance-decreasing coal is 1.0:0.25 through 1.0:3.0 or from the mixture of the coal mixture and other coal, by charging the coal blend into a coke oven, and by performing carbonization, it is possible to manufacture coke having a high strength and that, by at least controlling the proportion of the amount of large-permeation-distance coal to the whole coal mixture to be 30 mass % or less, it is possible to add large-permeation-distance coal without causing a decrease in strength with a higher degree of certainty. The proportions of the amount of other kinds of coal to the whole coal mixture may be desirably determined.

Here, when constant a and constant a' in the criteria [A] and [B] above are derived by determining permeation distance and the common logarithm log MF of Gieseler maximum fluidity MF, it is preferable to use coal having a log MF of more than 1.75 and less than 2.50, and it is preferable that the constant a and the constant a' be defined as the coefficient of log MF multiplied by values in the range of 0.7 or more and 1.0 or less, when a regression line that passes through the origin is drawn for the determined values. In the case of a coal brand having a small MF, since permeation distance is small, a measurement error tends to increase. Therefore, the lower limit of log MF is set to be more than 1.75.

It is possible to increase the blending ratio of coal corresponding to large-permeation-distance coal to a value larger than ever before without causing a decrease in the strength of coke which is manufactured from a coal blend containing a coal mixture prepared by blending large-permeation-distance coal and permeation-distance-decreasing coal so that, in terms of ratio between blending ratios, the relationship (large-permeation-distance coal):(permeation-distance-decreasing coal)=1.0:0.25 through 1.0:3.0 is satisfied.

Example 1

In order to conduct investigations regarding the additivity of large-permeation-distance coal and various coal brands, the permeation distance of various coal blends (coal mixtures) were determined. The properties of the coal brands used are given in Table 2.

TABLE 2

| | Coal Property | | | | |
|---|---|---|---|---|---|
| | Ro | logMF | TI | Ash | VM | Permeation distance |
| | | | | Unit | | |
| | % | log ddpm | vol. % | mass % d.b. | mass % d.b. | mm |
| Coal A | 0.80 | 4.00 | 17.3 | 8.9 | 35.9 | 21.5 |
| Coal B | 0.65 | 1.18 | 28.0 | 8.1 | 38.0 | 0.6 |
| Coal C | 0.72 | 2.40 | 14.0 | 9.1 | 35.9 | 9.4 |
| Coal D | 0.96 | 1.84 | 31.7 | 10.8 | 27.1 | 7.5 |
| Coal E | 0.99 | 2.06 | 33.8 | 8.5 | 28.5 | 7.8 |
| Coal F | 1.00 | 3.08 | 29.0 | 10.4 | 27.7 | 12.9 |
| Coal G | 1.29 | 0.48 | 42.4 | 7.6 | 20.8 | 2.0 |
| Coal H | 1.17 | 1.83 | 4.8 | 6.2 | 27.8 | 22.6 |
| Coal I | 1.12 | 3.33 | 26.0 | 9.0 | 24.5 | 10.6 |
| Coal J | 1.30 | 2.10 | 5.3 | 9.2 | 22.2 | 5.5 |
| Coal K | 1.36 | 2.33 | 26.0 | 10.5 | 21.4 | 13.1 |
| Coal L | 1.47 | 1.71 | 28.0 | 9.1 | 21.1 | 7.0 |
| Coal M | 1.53 | 0.30 | 34.3 | 10.2 | 16.9 | 0.2 |
| Coal N | 1.53 | 1.18 | 21.8 | 7.9 | 19.3 | 5.0 |
| Coal O | 1.55 | 1.41 | 16.3 | 9.5 | 18.7 | 3.5 |
| Coal P | 1.56 | 0.90 | 21.7 | 9.8 | 18.3 | 2.3 | d.b. refers to "on a dry basis".

"Ro" in Table 2 refers to the mean maximum vitrinite reflectance of coal prescribed in JIS M 8816.

"log MF" refers to the common logarithm of maximum fluidity (MF) determined by using a Gieseler plastometer method prescribed in JIS M 8801.

"Ash" (ash matter) and "VM" (volatile matter) are determined in accordance with "Methods for proximate analysis" prescribed in JIS M 8812.

"TI" refers to total inert amount (vol. %) calculated by the equation (X) above based on the Parr equation prescribed in JIS M 8816 "Solid mineral fuels-Methods of microscopical measurement for the macerals and reflectance" and its explanation.

The permeation distance of a coal blend was determined as roughly described hereafter. Coal blends (respectively denoted by "coal blend AB" through "coal blend AP") were prepared by blending coal A, which was a coal brand having an excessively large permeation distance, and each of the other coal B through coal P so that the blending ratio was 1:1 in terms of mass fraction on a dry basis. By using these coal blends as samples, and by using the apparatus illustrated in FIG. 1, permeation distance was determined. The container has a diameter of 20 mm and a height of 100 mm, and glass beads having a diameter of 2 mm were used as the material having through-holes penetrating from the upper surface to the lower surface. By weighing out, on a dry basis, 2.50 g of the coal sample pulverized to have a particle diameter of 2 mm or less, by charging the coal sample into the container, and by dropping a weight of 200 g onto the top of the coal sample 5 times with a falling length of 20 mm, the coal sample was packed (the thickness of the sample was 10 mm in this state). Subsequently, glass beads having a diameter of 2 mm were placed on the top of the packed layer of the sample 1 so that the thickness of the glass bead layer was 25 mm. Here, it is appropriate that the thickness of the glass bead layer be larger than a permeation distance. In the case where a thermoplastic material reaches the upper most surface of the glass bead layer when determination is performed, determination is performed again with an increased number of glass beads. The present inventors, by performing experiments with various thicknesses of a glass bead layer, confirmed that the same permeation distance is observed in the same sample as long as the thickness of a glass bead layer is larger than the permeation distance. A sillimanite disc having a diameter of 19 mm and a thickness of 5 mm was placed on the top of the glass bead packed layer, a quartz rod was placed as a dilatation-detecting rod on the disc, and a weight of 1.6 kg was placed on the top of the quartz rod. As a result, a pressure applied to the sillimanite disc was 50 kPa. By using nitrogen gas as an inert gas, heating was performed to a temperature of 550° C. at a heating rate of 3° C./min. By performing cooling in a nitrogen atmosphere after heating had been performed, the weights of beads which did not adhere to each other with thermoplastic coal were determined after having removing them from the cooled container.

The permeation distance was defined as the packing height of the glass bead packed layer in which beads adhered to each other. By having derived the relationship between the packing height and mass of the glass bead packed layer in advance, preparation was made so that it was possible to calculate the packing height of the glass bead packed layer from the weight of the beads to which the thermoplastic material adhered. As a result, equation (Y) below was derived, and permeation distance was calculated by equation (Y).

$$L=(G-M) \times H \quad (Y)$$

Here, L denotes the permeation distance [mm],
G denotes the mass [g] of the packed glass beads,
M denotes the mass [g] of beads which does not adhere to the thermoplastic material, and
H denotes the packing height per 1 g [mm/g] of the glass bead packed layer in the present experimental apparatus.

Here, in Table 3, the calculated weighted average values and determined values of the permeation distances of individual coal blends are given.

TABLE 3

| Item | Weighted Average Value (mm) | Determined Value (mm) | Determined Value − Weighted Average Value (mm) |
|---|---|---|---|
| Coal Blend AB | 11.0 | 10.7 | −0.3 |
| Coal Blend AC | 15.4 | 15.3 | −0.1 |
| Coal Blend AD | 14.5 | 13.3 | −1.2 |
| Coal Blend AE | 14.7 | 12.9 | −1.8 |
| Coal Blend AF | 17.2 | 16.4 | −0.8 |
| Coal Blend AG | 11.8 | 10.8 | −1.0 |
| Coal Blend AH | 22.1 | 23.0 | 0.9 |
| Coal Blend AI | 16.1 | 14.1 | −2.0 |
| Coal Blend AJ | 13.5 | 9.0 | −4.5 |
| Coal Blend AK | 17.3 | 11.4 | −5.9 |
| Coal Blend AL | 14.3 | 8.0 | −6.3 |
| Coal Blend AM | 10.9 | 8.8 | −2.1 |
| Coal Blend AN | 13.3 | 5.5 | −7.8 |
| Coal Blend AO | 12.5 | 2.7 | −9.8 |
| Coal Blend AP | 11.9 | 4.8 | −7.1 |

Figure 3:
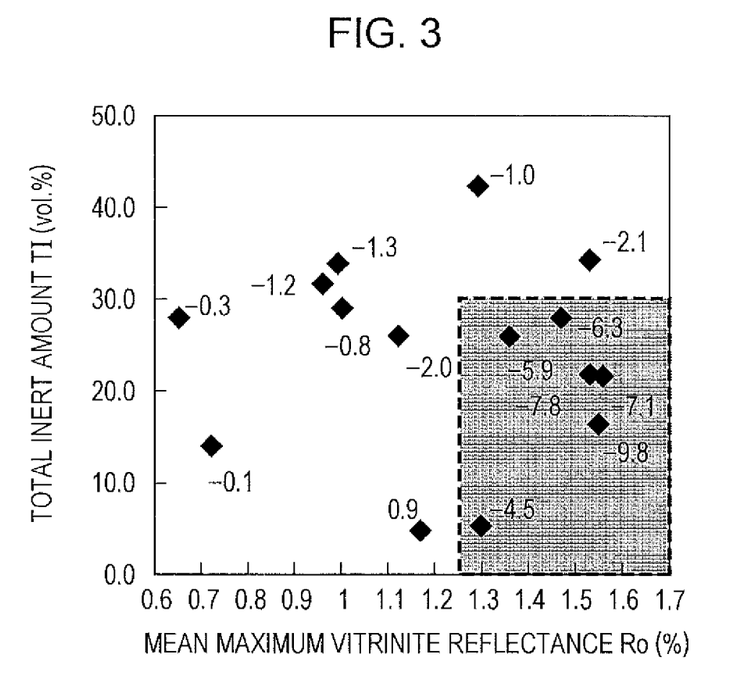
FIG. 3 is a graph illustrating the relationship between the mean maximum vitrinite reflectance Ro and total inert amount TI of coal B through coal P which were combined with coal A in the coal blends used in the EXAMPLE 1.

FIG. 3 illustrates the relationship between the mean maximum vitrinite reflectance Ro and total inert amount TI of coal B through coal P which were combined with coal A in the coal blends in order to prepare coal blend AB through coal blend AP. Each point on the graph in FIG. 3 is accompanied by a value indicating the difference (determined value−weighted average value) between the determined value of permeation distance and the weighted average value of permeation distances of individual constituent coal brands weighted by the blending ratios of the constituent coal brands of one of the coal blend AB through coal AP respectively containing coal B through coal P corresponding to the points. Among the constituent coal brands of the coal blend, the stronger the additivity of permeation distance, the more the difference between the determined value and the weighted average value approaches zero. However, as Table 3 and FIG. 3 indicate, in the case of a coal blend in which large-permeation-distance coal and coal having a mean maximum reflectance Ro of 1.25% or more and a volume fraction TI of 30% or less are combined, the difference takes a negative value having a comparatively large absolute value, which indicates that the additivity of permeation distance is not valid.

The reason for such a result is considered as follows. First, a permeation phenomenon in a thermoplastic process is influenced by the foaming phenomenon of coal which occurs because there is a decrease in the viscosity of thermoplastic coal and because gas generated inside the coal moves outside the coal. In addition, since coal (permeation-distance-decreasing coal) having a mean maximum reflectance Ro of 1.25% or more and a total inert amount TI of 30 vol. % or less, which has a high swelling pressure, has the function of compressing the surrounding particles. Therefore, it is considered that, in the case where such coal having a high swelling pressure and large-permeation-distance coal are adjacent to each other, since the coal having a high swelling pressure compresses and constrains the large-permeation-distance coal, the foaming phenomenon of the large-permeation-distance coal is inhibited. Here, although there is no problem even if the Ro of coal is large as long as the coal melts, since coal is less likely to melt in the case where Ro is excessively large, it is preferable that Ro be 1.25% or more and 1.70% or less, or more preferably 1.30% or more and 1.65% or less. The smaller the TI, the more likely the coal is to melt. Therefore, it is not necessary to put a limitation on the lower limit of TI. However, it is preferable that TI be 3 vol. % or more and 30 vol. % or less, or more preferably 5 vol. % or more and 28 vol. % or less.

Hereafter, it was evaluated whether it is possible to reduce the influence of large-permeation-distance coal, which decreases coke strength, in the case where coke is manufactured by blending large-permeation-distance coal and permeation-distance-decreasing coal at the same time in order to manufacture a coal blend. The evaluation was performed by using the following method. First, by using some of the coal brands given in Table 2, coal blends were manufactured respectively with various blending ratios of the coal brands. The blending ratios are given in Table 4.

wall temperature of 1050° C. for 6 hours with a weight of 10 kg being placed on the top of the coal blend, by removing the carbonized material from the furnace, and by cooling the carbonized material with nitrogen, coke was obtained. Regarding coke strength, in accordance with a drum strength testing method prescribed in JIS K 2151, by rotating a drum testing machine in which a specified amount of coke was charged at a rotational speed of 15 rpm for 150 cycles, and by then determining the mass fraction of coke particles having a particle diameter of 15 mm or more, drum strength DI (150/15), which indicates the ratio of the determined mass to the corresponding mass before rotation was per-

TABLE 4

| | Example/Comparative Example | | | | | | | | | | | | |
|---|---|---|---|---|---|---|---|---|---|---|---|---|---|
| | C1 | C2 | C3 | C4 | C5 | E1 | E2 | E3 | C6 | E4 | E5 | E6 | C7 |
| Blending Ratio of Coal A [mass %] | 0 | 5 | 10 | 15 | 0 | 10 | 20 | 30 | 0 | 12 | 20 | 30 | 40 |
| Blending Ratio of Coal B [mass %] | 2 | 5 | 1 | 0 | 0 | 0 | 0 | 0 | 9 | 5 | 0 | 0 | 2 |
| Blending Ratio of Coal C [mass %] | 3 | 1 | 1 | 1 | 1 | 1 | 1 | 1 | 3 | 5 | 1 | 3 | 3 |
| Blending Ratio of Coal D [mass %] | 2 | 0 | 6 | 5 | 0 | 0 | 0 | 0 | 3 | 0 | 0 | 0 | 5 |
| Blending Ratio of Coal E [mass %] | 34 | 29 | 28 | 29 | 51 | 51 | 43 | 38 | 20 | 35 | 61 | 42 | 16 |
| Blending Ratio of Coal F [mass %] | 43 | 34 | 33 | 20 | 40 | 23 | 15 | 0 | 50 | 25 | 1 | 0 | 0 |
| Blending Ratio of Coal G [mass %] | 5 | 12 | 12 | 19 | 0 | 5 | 13 | 18 | 0 | 0 | 0 | 10 | 19 |
| Blending Ratio of Coal I [mass %] | 6 | 12 | 6 | 11 | 0 | 2 | 0 | 5 | 0 | 0 | 2 | 0 | 0 |
| Blending Ratio of Coal M [mass %] | 5 | 2 | 3 | 0 | 0 | 0 | 0 | 0 | 0 | 0 | 0 | 0 | 0 |
| Blending Ratio of Coal N [mass %] | 0 | 0 | 0 | 0 | 8 | 8 | 8 | 8 | 15 | 18 | 15 | 15 | 15 |
| Blending Ratio of Coal N/Blending Ratio of Coal A [—] | — | 0 | 0 | 0 | — | 0.8 | 0.4 | 0.267 | — | 1.5 | 0.75 | 0.5 | 0.375 |
| Ro [%] | 1.029 | 1.027 | 1.026 | 1.031 | 1.035 | 1.031 | 1.033 | 1.034 | 1.036 | 1.036 | 1.033 | 1.036 | 1.036 |
| logMF [log ddpm] | 2.40 | 2.39 | 2.41 | 2.39 | 2.40 | 2.37 | 2.33 | 2.35 | 2.36 | 2.36 | 2.36 | 2.36 | 2.39 |
| VM [% d.b.] | 27.3 | 27.5 | 27.5 | 27.6 | 27.5 | 27.9 | 28.2 | 28.5 | 27.8 | 28.4 | 28.6 | 28.8 | 29.0 |
| DI 150/15 [—] | 84.1 | 84.0 | 83.8 | 83.2 | 84.3 | 84.2 | 84.0 | 83.9 | 84.4 | 84.3 | 84.3 | 84.0 | 83.3 |
| CSR [%] | 59.8 | 59.5 | 59.0 | 57.1 | 60.2 | 60.0 | 59.6 | 57.8 | 60.4 | 60.3 | 60.3 | 59.9 | 57.1 | d.b. refers to "on a dry basis".

Regarding symbols such as "CX" and "EX" (X denotes a natural number) in the row of "Example/Comparative Example" in Table 4, "CX" refers to "Comparative Example X", and "EX" refers to "Example X". In the cases of C1 through C7 and E1 through E6, coal blends were manufactured respectively with various blending ratios of the coal brands given in Table 2, and coke was manufactured by carbonizing each of the coal blends. In the cases of C1 through C7 and E1 through E6, the blending ratios of coal A through coal N were controlled so that the weighted average values of the properties, that is, weighted average values of Ro [%] and log MF [log ddpm] weighted by the respective blending ratios were almost the same, that is, the weighted average values of Ro of the coal blends were 1.026 to 1.036, and the weighted average values of log MF of the coal blends were 2.33 to 2.41.

Each of coal brands used for C1 through C7 and E1 through E6 was pulverized so that the particle diameter of 100 mass % of the coal particles was 3 mm or less, and the moisture content of each of the coal blends was controlled to be 8 mass %. By packing 16 kg of the coal blend into a carbonization can so that the bulk density was 750 kg/m$^3$, by carbonizing the coal blend in an electric furnace at a furnace formed, was calculated. In the row of "DI 150/15" in Table 4, the calculated drum strength DI (150/15) is given as the determined result of coke strength.

In C1 through C7 and E1 through E6, coal A is large-permeation-distance coal, and coal N is permeation-distance decreasing coal. As coal brands other than coal A and coal N, coal brands which were not classified as large-permeation-distance coal or permeation-distance-decreasing coal were selected. First, since the permeation distance (21.5 mm) of coal A was larger than the permeation distance (17.9 mm) which was calculated by substituting the value of the log MF of coal A into equation [I] in which a was assigned a value of 3.44, that is, the coefficient of the linear regression formula that passing through the origin derived from the determined values of common logarithm of Gieseler maximum fluidity and permeation distance of coal brands in Table 4 having a log MF of less than 2.5, coal A was judged as large-permeation-distance coal on the basis of criteria [A]. Also, since the permeation distance of coal A was larger than the permeation distance (16.8 mm) which was calculated by equation [II] in which a' was assigned a value of 3.44, that is, the coefficient of the linear regression formula described above and in which b was assigned the value 5 times the standard deviation (0.6) of the permeation distances determined as described above, coal A was judged as large-permeation-distance coal on the basis of criteria [B]. The permeation distance of coal A, which was determined through steps (1) through (4) described above by using the determining apparatus 30 illustrated in FIG. 1, was larger than 15 mm. Therefore, coal A was within any one of the ranges according to criteria [A], [B], and [C] above, which indicate the ranges of large-permeation-distance coal. In addition, it can be said that coal N, which satisfied the conditions that the mean maximum vitrinite reflectance Ro is 1.25% or more and the total inert amount TI in a petrographic analysis is 30 vol. % or less, is permeation-distance-decreasing coal. The blending ratios of the respective coal brands are given in Table 4.

In the cases of E1 through E6, by respectively varying the blending ratios of coal A and coal N, and by carbonizing coal blends within the range according to the present disclosure, the corresponding kinds of coke were manufactured. In the cases of C1 through C7, by carbonizing coal blends out of the range according to the present disclosure, the corresponding kinds of coke were manufactured.

In the conventional coal blending theory for estimating, from the properties of coal, coke strength after carbonization, it has been considered that coke strength is determined mainly by vitrinite mean maximum reflectance Ro of coal and the logarithm log MF of Gieseler maximum fluidity MF (for example, refer to Non Patent Literature 4). Therefore, on the basis of such theory, it is expected that the coal blends corresponding to C1 through C7 and E1 through E6 have almost the same coke strength. In addition, in accordance with Patent Literature 1, it is expected that there is a decrease in coke strength in the case where there is an increase in the blending ratio of coal A, which is large-permeation-distance coal.

Figure 4:
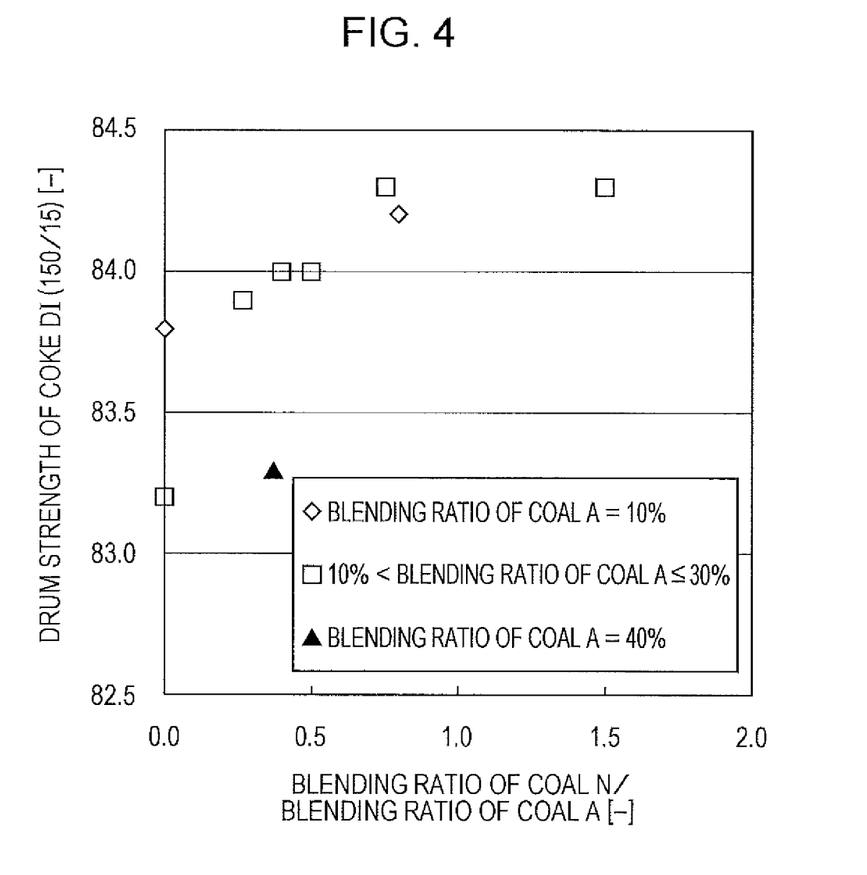
FIG. 4 is a graph illustrating the relationship between the ratio of the blending ratio of coal N to the blending ratio of coal A in the coal blends used in the EXAMPLE 1 and the drum strength DI (150/15) of coke.

FIG. 4 is a graph illustrating, by classifying for each blending ratio of coal A, the relationship between the ratio of the blending ratio of coal N to the blending ratio of coal A and the drum strength DI (150/15) of coke in the cases of C1 through C7 and E1 through E6 in Table 4. As C1 through C4 indicate, although the drum strength DI of coke (coke strength) was large, that is, 83.8 or more even though coal N was not added in the case where the blending ratio of coal A was 10 mass % or less, there was a decrease in coke strength in the case where the blending ratio of coal A was 15 mass %, that is, more than 10 mass %. On the other hand, according to the graph in FIG. 4, it is clarified that there was an increase in coke strength in the case where coal N is blended in combination with coal A. It is clarified that, at this time, it is possible to manufacture coke having a high strength in the case where coal N is added so that the ratio of the mass of coal N to the mass of coal A is about 0.25 or more and in the case where the blending ratio of coal A is 30 mass % or less. In addition, on the basis of the comparison between E6 and C7, it is clarified that, in the case where the blending ratio of coal A is 40 mass %, there is a decrease in coke strength even if coal N is added. Therefore, it is clarified that it is possible to reduce the influence of large-permeation-distance coal, which decreases coke strength, in the case where coke is manufactured by blending large-permeation-distance coal and coal (permeation-distance-decreasing coal) having a mean maximum vitrinite reflectance Ro of 1.25% or more and a total inert amount TI of 30 vol. % or less at the same time in order to manufacture a coal blend. In the cases of E2, E3, E5 and E6, although the blending ratio of large-permeation-distance coal, that is, coal A is larger than in the case of C4, permeation-distance-decreasing coal, that is, coal N is added, and the ratio (blending ratio of coal N/blending ratio of coal A) is 0.25 to 3.0 in any case. It is clarified that, in the case where a coal blend containing a coal mixture corresponding to one of E2, E3, E5 and E6 is used as a raw material for coke making, it is possible to manufacture coke having a high strength and that a mixture having such a composition is useful as a coal mixture for coke making.

In addition, from the results of E1 through E6, it is confirmed that, by increasing the blending ratio of permeation-distance-decreasing coal, it is possible to increase the blending ratio of large-permeation-distance coal, that is, coal A to about 30 mass % at maximum without significantly decreasing coke strength under the condition that the ratio of the blending ratio of permeation-distance-decreasing coal, that is, coal N to the blending ratio of large-permeation-distance coal, that is, coal A is 0.25 or more.

From the results of the EXAMPLE 1, it is clarified that, by using large-permeation-distance coal, which causes a decrease in coke strength, and permeation-distance-decreasing coal in combination, it is possible to maintain a high level of coke strength after carbonization has been performed.

Example 2

Hereafter, investigations regarding the preferable value of the ratio of the blending ratio of permeation-distance-decreasing coal to the blending ratio of large-permeation-distance coal were conducted. By selecting coal Q (having a mean maximum vitrinite reflectance Ro of 1.56%, a total inert amount TI of 21.7 vol. %, and a permeation distance of 2.1 mm) as permeation-distance-decreasing coal (having a mean maximum vitrinite reflectance Ro of 1.25% or more and a total inert amount TI of 30 vol. % or less), and by selecting coal R (having a permeation distance of 19.2 mm) as large-permeation-distance coal, the permeation distances of coal blends having various blending ratios of the respective coal brands were determined. The results are given in Table 5.

TABLE 5

| Blending Ratio of Coal Q [%] | Blending Ratio of Coal R [%] | Blending Ratio of Coal Q/ Blending Ratio of Coal R [—] | Determined Permeation Distance [mm] | Weighted Average Permeation Distance [mm] | Permeation Distance Ratio [—] | Difference between Weighted Average Permeation Distance and Determined Permeation Distance [mm] |
|---|---|---|---|---|---|---|
| 0 | 100 | 0 | 19.2 | 19.2 | 1.00 | 0 |
| 20 | 80 | 0.25 | 10.3 | 15.8 | 0.65 | 5.5 |
| 25 | 75 | 0.33 | 8.9 | 14.9 | 0.60 | 6.0 |
| 50 | 50 | 1.0 | 4.4 | 10.7 | 0.41 | 6.3 |

TABLE 5-continued

| Blending Ratio of Coal Q [%] | Blending Ratio of Coal R [%] | Blending Ratio of Coal Q/ Blending Ratio of Coal R [—] | Determined Permeation Distance [mm] | Weighted Average Permeation Distance [mm] | Permeation Distance Ratio [—] | Difference between Weighted Average Permeation Distance and Determined Permeation Distance [mm] |
|---|---|---|---|---|---|---|
| 67 | 33 | 2.0 | 2.9 | 7.7 | 0.37 | 4.8 |
| 75 | 25 | 3.0 | 2.7 | 6.4 | 0.42 | 3.7 |
| 100 | 0 | — | 2.1 | 2.1 | 1.00 | 0 |

"Permeation Distance Ratio" in Table 5 refers to the ratio [-] of the determined permeation distance to the weighted average permeation distance.

Figure 5:
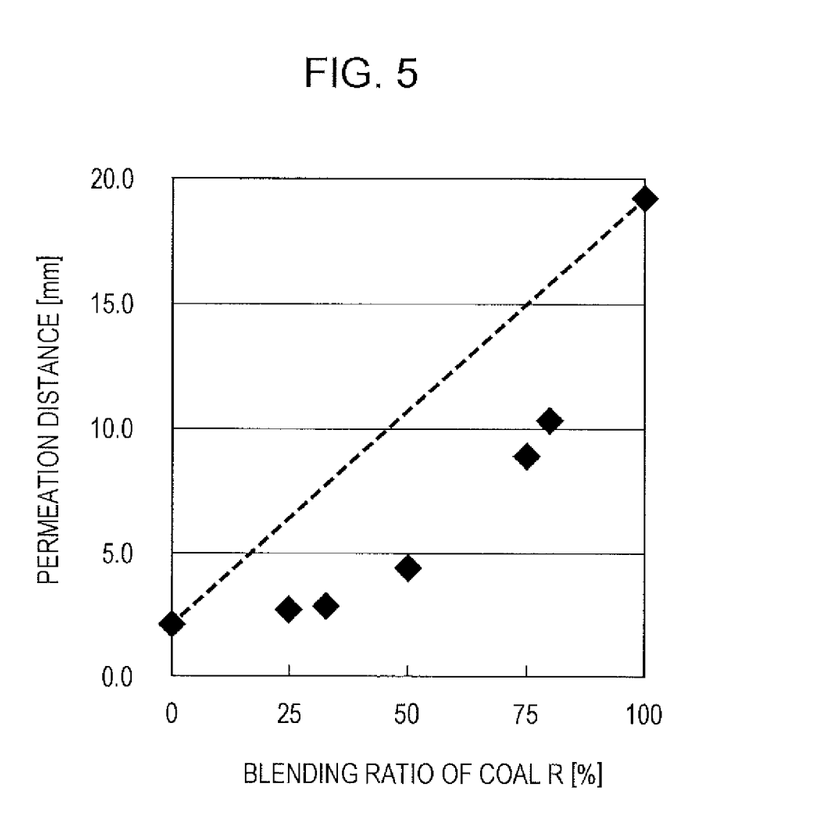
FIG. 5 is a graph illustrating the relationship between the blending ratio of coal R in the coal blends used in the EXAMPLE 2 and the determined permeation distance of the coal blends.

FIG. 5 illustrates the relationship between the blending ratio of coal R and the determined permeation distance. The dashed line in FIG. 5 indicates the weighted average value of the permeation distances of coal Q and coal R weighted by the blending ratios of coal Q and coal R. As Table 5 and FIG. 5 indicate, although the determined permeation distance increased with increasing blending ratio of large-permeation-distance coal, that is, coal R, the determined permeation distance was considerably smaller than the weighted average value of permeation distance. Therefore, as Table 5 and FIG. 5 indicate, it is clarified that a tendency for the permeation distance of the coal blend to increase due to coal R (large-permeation-distance coal) was reduced by coal Q (permeation-distance-decreasing coal).

Figure 6:
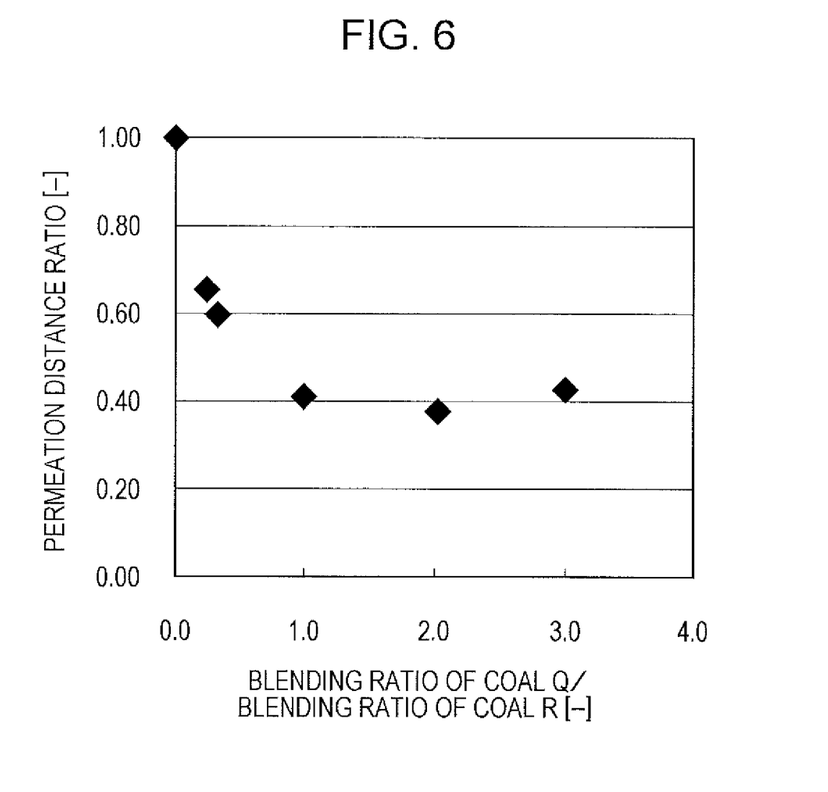
FIG. 6 is a graph illustrating the relationship between the ratio of the blending ratio of coal Q to the blending ratio of coal R in the coal blends used in the EXAMPLE 2 and the permeation distance ratio.

FIG. 6 illustrates the relationship between the ratio [-] (blending ratio of coal Q/blending ratio of coal R) and the permeation distance ratio [-] (=determined permeation distance/weighted average value of permeation distance). As FIG. 6 indicates, it is clarified that the determined permeation distance was about 0.4 to 0.7 times the weighted average of permeation distance in the case where the ratio (blending ratio of coal Q/blending ratio of coal R), that is, the ratio of the mass fraction of the permeation-distance-decreasing coal to the mass fraction of large-permeation-distance coal was 0.25 to 3.0, which means that a tendency for the permeation distance of the coal blend to increase was significantly reduced. Although the permeation distance ratio did not rapidly increase in the case where the ratio of blending ratio was more than 3.0, the amount of large-permeation-distance coal was relatively small in the case where the ratio of blending ratio was large. Therefore, since the weighted average value of permeation distance is small, there is a decrease in negative effect due to large-permeation-distance coal being contained in the coal blend. Moreover, since it is impractical that the blending ratio of permeation-distance-decreasing coal be excessively large, it is appropriate that the ratio of blending ratio be 3.0 or less.

As described above, it is clarified that, by controlling the total blending ratio of coal brands having a mean maximum vitrinite reflectance Ro of 1.25% or more and a total inert amount TI of 30 vol. % or less to be 0.25 to 3.0 times the total blending ratio of large-permeation-distance coal in a coal blend (coal mixture), it is possible to strongly reduce a tendency for the permeation distance of the coal blend to increase, it is possible to inhibit a decrease in the strength of coke which is manufactured by carbonizing the coal blend, and it is possible to maintain a high level of coke strength.

It is clarified that, by using large-permeation-distance coal and permeation-distance-decreasing coal in combination, the permeation distance of the coal blend (coal mixture) is decreased to a value equal to or less than the average value. In the case where large-permeation-distance coal is used as a raw material for coke, although a coal mixture (coal blend) may be prepared by controlling the blending ratios of the large-permeation-distance coal and permeation-distance-decreasing coal as was done in the EXAMPLE 1, a coal blend to be charged into a coke oven may be prepared by preparing a coal mixture in which the large-permeation-distance coal and the permeation-distance-decreasing coal are mixed in advance and by blending the coal mixture with other raw materials such as other coal brands in a coke factory. In the case where it is possible to obtain both large-permeation-distance coal and permeation-distance-decreasing coal, for example, in a coal mining area or in a coal center, a coal mixture may be prepared there. As described above, by preparing in advance a coal mixture which can preferably be used as a raw material for coke making, it is possible to obtain preferable coal for coke making without considering the blending ratios of large-permeation-distance coal and permeation-distance-decreasing coal in a coke factory. As described above, by using the method according to the present disclosure, it is possible to use, as a raw material for coke, large-permeation-distance coal which causes a decrease in coke strength in the case where an appropriate amount of permeation-distance-decreasing coal is not used at the same time, with ease, in a large amount, and with low cost as a result of preventing pulverizing costs from increasing.

REFERENCE SIGNS LIST

1 sample
2 material having through-holes penetrating from the upper surface to the lower surface
3 container
5 sleeve
7 thermometer
8 heating device
9 temperature detector
10 temperature controller
11 gas inlet port
12 gas outlet port
30 permeation distance-determining apparatus (constant load)
31 loading device (constant load)
32 weight
33 dilatation-detecting rod
34 displacement sensor
40 permeation distance-determining apparatus (constant volume)
41 loading device (loading while maintaining constant volume)
42 pressure-detecting rod
43 load cell

The invention claimed is:

1. A coal mixture comprising:
   large-permeation-distance coal; and
   permeation-distance-decreasing coal,
   wherein:
      a mass fraction of the permeation-distance-decreasing coal in the coal mixture is in a range derived by multiplying a mass fraction of the large-permeation-distance coal by 0.25 or more and 3.0 or less,
      the permeation-distance-decreasing coal has a mean maximum vitrinite reflectance Ro of 1.25% or more and a total inert amount TI of 30 vol. % or less,
      the permeation-distance-decreasing coal makes a permeation distance of a 1:1 coal mixture of the permeation-distance-decreasing coal and the large-permeation-distance coal smaller than or equal to a value calculated by multiplying a weighted average value by a constant 0.67, the weighted average value being calculated from permeation distances of the large-permeation-distance coal and the permeation-distance-decreasing coal at a mass ratio of 1:1 thereof,
      the large-permeation-distance coal has a permeation distance (mm) that is determined by the following steps:
         placing a material having through-holes penetrating from an upper surface to a lower surface of the material on the top of a coal sample packed in a container;
         heating the coal sample to permeate into the through-holes; and
         determining a distance over which the coal permeates into the through-holes as the permeation distance (mm), and
      the permeation distance (mm) of the large-permeation-distance coal is more than a value of criteria permeation distance derived by using the following equation [I]:

$$\text{criteria permeation distance} = 1.3 \times a \times \log MF \quad [\text{I}]$$

where MF is the Gieseler maximum fluidity (ddpm) of coal, and a is a constant defined as a coefficient of the common logarithm log MF of Gieseler maximum fluidity MF multiplied by a value in the range of 0.7 or more and 1.0 or less, when a regression line that passes through the origin is drawn based on data sets of the determined value of permeation distance (mm) and log MF of at least one of coal brands having a log MF of less than 2.5.

2. The coal mixture according to claim 1, wherein the constant a is a constant defined as a coefficient of the common logarithm log MF of Gieseler maximum fluidity MF multiplied by a value in the range of 0.7 or more and 1.0 or less, when a regression line that passes through the origin is drawn based on data sets of the determined value of permeation distance (mm) and log MF of at least one of coal brands having a log MF of more than 1.75 and less than 2.50.

3. The coal mixture according to claim 1, wherein a content of the large-permeation-distance coal in the coal mixture is 30 mass % or less.

4. A method for manufacturing the coal mixture according to claim 1, the method comprising the steps of:
   preparing the large-permeation-distance coal and the permeation-distance-decreasing coal; and
   mixing the large-permeation-distance coal and the permeation-distance-decreasing coal so that a content of the permeation-distance-decreasing coal in the coal mixture is in a range derived by multiplying a content of the large-permeation-distance coal in the coal mixture by 0.25 or more and 3.0 or less.

5. A method for manufacturing coke, the method comprising coking the coal mixture according to claim 1 as a raw material for the coke by:
   preparing a coal blend from the coal mixture or a mixture of the coal mixture and other coal;
   charging the coal blend into a coke oven; and
   performing carbonization on the charged coal blend to form coke.

6. A coal mixture comprising:
   large-permeation-distance coal; and
   permeation-distance-decreasing coal,
   wherein:
      a mass fraction of the permeation-distance-decreasing coal in the coal mixture is in a range derived by multiplying a mass fraction of the large-permeation-distance coal by 0.25 or more and 3.0 or less,
      the permeation-distance-decreasing coal has a mean maximum vitrinite reflectance Ro of 1.25% or more and a total inert amount TI of 30 vol. % or less,
      the permeation-distance-decreasing coal makes a permeation distance of a 1:1 coal mixture of the permeation-distance-decreasing coal and the large-permeation-distance coal smaller than or equal to a value calculated by multiplying a weighted average value by a constant 0.67, the weighted average value being calculated from permeation distances of the large-permeation-distance coal and the permeation-distance-decreasing coal at a mass ratio of 1:1 thereof,
      the large-permeation-distance coal has a permeation distance (mm) that is determined by the following steps:
         placing a material having through-holes penetrating from an upper surface to a lower surface of the material on the top of a coal sample packed in a container;
         heating the coal sample to permeate into the through-holes; and
         determining a distance over which the coal permeates into the through-holes as the permeation distance (mm), and
      the permeation distance (mm) of the large-permeation-distance coal is more than a value of criteria permeation distance derived by using the following equation [II]:

$$\text{criteria permeation distance} = a' \times \log MF + b \quad [\text{II}],$$

where MF is the Gieseler maximum fluidity (ddpm) of the coal,
      a' is a constant defined as a coefficient of the common logarithm log MF of a Gieseler maximum fluidity MF multiplied by a value in the range of 0.7 or more and 1.0 or less, when a regression line that passes through the origin is drawn based on data sets of the determined value of permeation distance (mm) and log MF of at least one of coal brands having a log MF of less than 2.5, and
      b is a constant defined as a value equal to or more than the average value of the standard deviation of permeation distance and equal to or less than a value derived by multiplying the average value by 5, when determination is performed plural times for the same sample of one or more kinds of coal selected from among the coal brands which are used for deriving the regression line.

7. The coal mixture according to claim 6, wherein the constant a' is a constant defined as a coefficient of the common logarithm log MF of Gieseler maximum fluidity MF multiplied by a value in the range of 0.7 or more and 1.0 or less, when a regression line is drawn based on data sets of the determined value of permeation distance (mm) and log MF of at least one of coal brands having a log MF of more than 1.75 and less than 2.50.

8. The coal mixture according to claim 6, wherein the content of the large-permeation-distance coal in the coal mixture is 30 mass % or less.

9. A method for manufacturing the coal mixture according to claim 6, the method comprising the steps of:
   preparing the large-permeation-distance coal and the permeation-distance-decreasing coal; and
   mixing the large-permeation-distance coal and the permeation-distance-decreasing coal so that a content of the permeation-distance-decreasing coal in the coal mixture is in a range derived by multiplying a content of the large-permeation-distance coal in the coal mixture by 0.25 or more and 3.0 or less.

10. A method for manufacturing coke, the method comprising coking the coal mixture according to claim 6 as a raw material for the coke by:
    preparing a coal blend from the coal mixture or a mixture of the coal mixture and other coal;
    charging the coal blend into a coke oven; and
    performing carbonization on the charged coal blend to form coke.

11. A coal mixture comprising:
    large-permeation-distance coal; and
    permeation-distance-decreasing coal,
    wherein:
        a mass fraction of the permeation-distance-decreasing coal in the coal mixture is in a range derived by multiplying a mass fraction of the large-permeation-distance coal by 0.25 or more and 3.0 or less,
        the permeation-distance-decreasing coal has a mean maximum vitrinite reflectance Ro of 1.25% or more and a total inert amount TI of 30 vol. % or less,
        the permeation-distance-decreasing coal makes a permeation distance of a 1:1 coal mixture of the permeation-distance-decreasing coal and the large-permeation-distance coal smaller than or equal to a value calculated by multiplying a weighted average value by a constant 0.67, the weighted average value being calculated from permeation distances of the large-permeation-distance coal and the permeation-distance-decreasing coal at a mass ratio of 1:1 thereof, and
        the large-permeation-distance coal has a permeation distance (mm) of 15 mm or more, the permeation distance being determined by the following steps (1) to (4):
        (1) preparing a coal sample by pulverizing coal so that particles having a particle diameter of 2 mm or less constitute 100 mass % of the coal sample and packing the pulverized coal into a container so that a bulk density is 0.8 g/cm$^3$ and a layer thickness is 10 mm,
        (2) placing glass beads having a diameter of 2 mm on the top of the coal sample so that the thickness of a glass bead layer is more than or equal to a permeation distance;
        (3) heating the coal sample from room temperature to a temperature of 550° C. at a heating rate of 3° C./min in an inert gas atmosphere with a load of 50 kPa being applied to the top of the glass bead layer so that the coal sample melts and permeates into the glass bead layer, and
        (4) determining the permeation distance (mm) of the coal sample which has permeated into the glass bead layer.

12. The coal mixture according to claim 11, wherein the content of the large-permeation-distance coal in the coal mixture is 30 mass % or less.

13. A method for manufacturing the coal mixture according to claim 11, the method comprising the steps of:
    preparing the large-permeation-distance coal and the permeation-distance-decreasing coal; and
    mixing the large-permeation-distance coal and the permeation-distance-decreasing coal so that a content of the permeation-distance-decreasing coal in the coal mixture is in a range derived by multiplying a content of the large-permeation-distance coal in the coal mixture by 0.25 or more and 3.0 or less.

14. A method for manufacturing coke, the method comprising coking the coal mixture according to claim 11 as a raw material for the coke by:
    preparing a coal blend from the coal mixture or a mixture of the coal mixture and other coal;
    charging the coal blend into a coke oven; and
    performing carbonization on the charged coal blend to form coke.

* * * * *